United States Patent [19]

Helmer

[11] 4,043,906
[45] Aug. 23, 1977

[54] METHOD AND APPARATUS FOR REDUCING THE TRANSIENT EFFECTS OF LIQUID COMPRESSIBILITY IN A LIQUID CHROMATOGRAPHY SYSTEM

[75] Inventor: John Colville Helmer, Menlo Park, Calif.

[73] Assignee: Varian Associates, Inc., Palo Alto, Calif.

[21] Appl. No.: 668,340

[22] Filed: Mar. 18, 1976

[51] Int. Cl.$^2$ .............................................. B01D 15/08
[52] U.S. Cl. .............................. 210/31 C; 137/101.21; 210/137; 210/198 C; 73/61.1 C
[58] Field of Search ............... 210/22 R, 97, 134, 137, 210/198 C, 31 C; 73/61.1 C; 137/2, 12, 101.21, 568

[56] References Cited

U.S. PATENT DOCUMENTS

| | | | |
|---|---|---|---|
| 1,942,793 | 1/1934 | Bailey | 137/101.21 X |
| 2,899,969 | 8/1959 | Kirby | 137/12 X |
| 3,446,057 | 5/1969 | Bakalyar et al. | 210/198 C |
| 3,612,085 | 10/1971 | Clark | 137/12 |
| 3,855,129 | 12/1974 | Abrahams et al. | 210/198 C |
| 3,917,531 | 11/1975 | Magnussen | 210/198 C |
| 3,934,456 | 1/1976 | Munk | 210/198 C |

OTHER PUBLICATIONS

Instruments in Chemical Engineering, June 12, 1961, p. 116.

Primary Examiner—John Adee
Attorney, Agent, or Firm—Stanley Z. Cole; Gerald M. Fisher; John J. Morrissey

[57] ABSTRACT

Method and apparatus for damping oscillatory behavior and reducing the effective time constant incident to reattainment of equilibrium pressure and flow following a change in fluid pressure or flow rate in a liquid chromatography system. The system may include a chromatographic column, a reservoir for a slightly compressible liquid mobile phase, and piston means cooperating with the reservoir and normally driven at a velocity which is constant over a given time interval, for enabling pumping of the mobile liquid phase through the chromatographic column. In accordance with the invention, a transient velocity component is superimposed upon the constant velocity component of the mobile liquid phase caused by the piston motion. The transient velocity component is proportional to the reservoir volume and to the time derivative of pressure in the reservoir. The additionally imparted motion damps the transient oscillations that arise from any pressure change imposed on the slightly compressible liquid phase. Such pressure changes may e.g., be induced during operation of the chromatography system in a gradient elution mode.

24 Claims, 2 Drawing Figures

METHOD AND APPARATUS FOR REDUCING THE TRANSIENT EFFECTS OF LIQUID COMPRESSIBILITY IN A LIQUID CHROMATOGRAPHY SYSTEM

BACKGROUND OF INVENTION

This invention relates generally to chromatography systems and more specifically to liquid chromatography systems, particularly those in which so-called gradient elution techniques are employed.

In the course of carrying out liquid chromatography methods, particularly where high-pressure liquid chromatography is practiced with relatively large reservoirs (e.g., in excess of about 10 ml), it is found that the time constant incident to reattainment of equilibrium following a sudden pressure change in the system, can be of the order of several minutes, e.g., typically 1 to 6 minutes. The sudden pressure change noted can arise e.g., in consequence of a programmed change in flow rate, or in consequence of practicing gradient elution techniques, i.e., the use of a solvent mixture with continuously changing concentration ratio — where the source of the pressure change phenomenon is the variation in viscosity with change in relative concentration of the components. These oscillatory effects are all driven by the expansion and compression of the solvents in the reservoir or reservoirs, i.e., the oscillatory effects are ultimately caused by the fact that the solvents, although not always so though of, are indeed slightly compressible.

The normal and usual arrangement in chromatography apparatus of the type considered herein entails use of one or more reservoirs, which are basically in the nature of syringe pumps. A given reservoir thus may comprise a cylindrical tube or the like, having a volume V. A piston of circular cross-section is mounted for axially directed movement in the cylinder, and is normally driven by motor means at a velocity v, which is constant over a given time interval to provide a constant average flow rate $Q_o$ for the liquid mobile phase present within the reservoir. Assuming, however, that for the reasons mentioned above a sudden pressure change is effected, the compressibility k of the liquid causes a transient change from the average flow rate $Q_o$ for the liquid phase flowing out of the reservoir, the transient flow rate $Q_t$ of the flow being in accordance with the equation:

$$Q_t = (-KV)(dP/dt), \quad (1)$$

where $k$ is the fluid compressibility, V is the reservoir volume, and $dP/dt$ is the time derivative of pressure in the reservoir. It can be seen from equation (1) that a sudden increase or decrease in P cause the volume of the liquid phase to transiently contract or expand, due to the compressibility of the liquid phase thereby causing the transient change in the flow rate.

The net effect of the foregoing phenomena is one of providing erroneous concentration variations at the output of the fluid mixer. These concentrations variations can interact with the chromatographic column to produce additional pressure changes which reinforce the initial pressure disturbance, thereby generating a continuing instability or oscillation.

In accordance with the foregoing, it may be regarded as an object of the present invention to provide method and apparatus for use with liquid chromatography systems, which reduce the effectivetime constant incident to reattainment of equilibrium pressure and flow, and thereby damp the oscillatory behavior following a change in fluid pressure of the system.

SUMMARY OF INVENTION

In accordance with the present invention, the foregoing objects, and others as will become apparent in the course of the ensuing specification, are achieved by introducing modifications to a liquid chromatography system which function to reduce the effective time constant incident to reattainment of equilibrium pressure and flow, and thereby damp oscillatory behavoir following a change in fluid pressure in the system.

The systems of the type considered herein are normally characterized by the inclusion of a chromatographic column, a reservoir for a slightly compressible liquid mobile phase, and piston means that cooperates with the reservoir and is normally driven at a velocity, $v$, which in general is such as to reproduce a desired gradient—and which can be regarded as constant over a time interval of appropriate duration so as to enable pumping of the mobile liquid phase at a constant average flow rate $Q_o$ through the chromatographic column. In accordance with the present invention, an additional velocity component which is proportional to the volume of the reservoir and to the time derivative of pressure at the reservoir, is superimposed upon the piston motion. The additionally imparted motion serves to damp the transient oscillations that arise from pressure changes imposed on the slightly compressible liquid phase, e.g., in consequence of operation of the chromatography system in a gradient elution mode.

In one apparatus embodiment of the invention, an electronic feedback loop is provided for the motor drive of the aforementioned piston, the feedback signal being of such character as to enable the desired superimposed velocity component. The loop may thus include means for generating a signal proportional to the time derivative of the system pressure acting upon the reservoir, means for amplifying the signal in proportion to the reservoir volume, and means for coupling the amplified signal in feedback relationship to the speed control of the aforementioned motor means. where (as is usual in gradient liquid chromatography systems) a pair of such reservoirs and piston pumps are provided, the signal indicative of the time derivative of the pressure may thus be taken from a point between the fluid mixer and the chromatographic column, with the velocity of each pump piston being modified in the manner indicated.

BRIEF DESCRIPTION OF DRAWINGS

The invention is diagrammatically illustrated, by way of example, in the drawing appended hereto, in which.

DESCRIPTION OF PREFERRED EMBODIMENT

Figure 1:
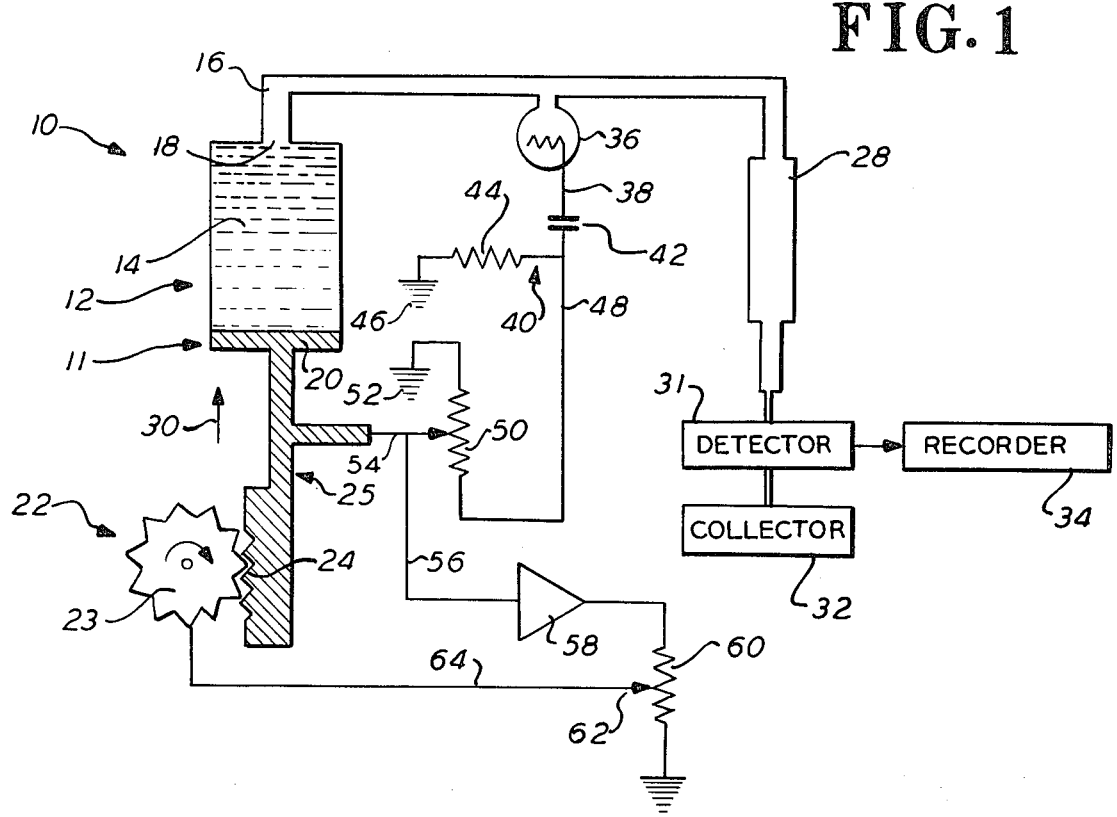
FIG. 1 schematically illustrates key elements of a signal reservoir liquid chromatography system incorporating the features of the present invention.

In FIG. 1 a schematic diagram is set forth which illustrates in a highly simplified fashion the manner in which the present invention may be applied to a single reservoir liquid chromatography system 10. The system 10, which can be of the so-called high-pressure liquid chromatography (HPLC) type, includes basic elements which are well-known in the prior art. In particular, a syringe pump 11 is provided, which includes a reservoir 12, which may be a cylindrical tube. The reservoir 12 may have a relatively large volume V, exceeding 100 ml. A liquid mobile phase 14 is contained within reservoir 12, and is pumped or expelled through tubing 16 processing from reservoir outlet 18 in consequence of axially directed movement 30 of a piston 20 into the reservoir. The piston 20 is normally driven at a velocity $v$ by a motor means 22, the drive gear 23 of which engages a rack 24 on an axially projecting piston rod 25. Assuming for purposes of analysis that $v$ is constant over a time interval of suitable duration, the liquid 14 is thus normally pumped from reservoir 12 at an average constant flow rate $Q_o$, and thence passes through tubing 16 to a conventional chromatographic column 28.

It will, of course, be understood that liquid 14 constitutes the mobile liquid phase, i.e., a solvent utilized in a chromatographic separation process; and further, as is also known in the present art, that the output from column 28 may be provided to a detector 31 and a collector 32; and that the detector 31 may be associated with a suitable recorder 34.

For purposes of simplifying explanation of the present invention, the depiction of FIG. 1 illustrates use of a simple one-component mobile phase. It will be understood, however, that the invention is applicable and indeed will be widely used with chromatography systems operating in a so-called gradient elution mode, and that in such instances various arrangements known in the art may be utilized. For example, a first solvent from reservoir 12 may be fed into an inline mixer wherein the first solvent is mixed with a second solvent in a desired concentration ratio, which ratio may be made to vary in accordance with a predetermined program. In this sort of arrangement, for example, reservoir 12 may hold water, and methenol or the like may be fed into the mixer.

The two reservoir gradient liquid chromatography (L.C.) systems will be further discussed in connection with FIG. 2 hereinbelow. Regardless, however, of whether one reservoir (as in FIG. 1) is utilized, or whether a pair of reservoirs (as in FIG. 2) is employed, the principles of the invention are such that each piston velocity is modified as indicated hereinafter. In particular, and continuing to refer to FIG. 1, the "normal" velocity $v$ of forward movement 30 of piston 20 is modified by imposition on such motion of an additional component, which is not constant, but rather is proportional to the time derivative of pressure at reservoir 12, and also to the volume V of reservoir 12. A simple electronic arrangement enabling the aforementioned result is illustrated in FIG. 1.

In particular, a pressure gauge 36 is provided, which is seen to be so positioned as to be responsive to the pressure at the output of reservoir 12 — or alternatively in 1 this may be viewed as the pressure at the input of chromatographic column 28. Pressure gauge 36 may, for example, be a strain gauge operating on piezoelectric princples. Other types of sensitive pressure gauges may similarly be utilized, which yield outputs in an electrical form suitable for further manipulation.

The electrical signal proceeding from gauge 36 at line 38 is, in accordance with the invention, provided to a differentiating network 40 consisting of a capacitor 42 and a resistor 44, the latter being connected to ground at 46. Thus, the electrical signal at 38 is proportional to pressure, and the differentiated signal proceeding from network 40 at line 48, is proportional to the time derivative of pressure i.e. $dP/dt$. The ensuing differentiated signal thence passes through a slide wire resistor 50, which is connected to ground at 52.

The contact arm 54 for slide wire resistor 50 is seen directly linked to piston rod 25 (for movement therewith), so that the contact arm 54 is displaced along with the movement of the piston. Thus, a resistance is placed in series with line 48, which is in accordance with the axial position of piston 20; The inserted series resistance is thus proportional to the volume V of reservoir 12. Accordingly, the signal in line 56 proceeding from contact arm 54 is of the form V $(dP/dt)$. This signal is then passed to an amplifier 58, and thence proceeds through a further slide wire resistor 60.

The contact arm 62 for resistor 60 is adjusted to provide a suitable proportionality constant. In particular, the arm 62 is so set that the signal furnished at line 64, which constitutes the final portion of a feedback loop to motor means 22, is equal to the expression $kV (dP/dt)$. Thus, the arrangement illustrated in FIG. 1 is such that the velocity of piston 20 in the direction 30 is modified by the feedback signal — which, being of the form indicated, precisely cancels out the transient flow generated in accordance with equation (1) above.

Consideration of the physical phenomena occurring in system 10, further illustrates the underlying mechanism of the invention, and the general mode of its application. In particular, and as previously indicated by equation (1), a sudden pressurre change, induced, e.g., by viscosity changes where gradient elution is practiced, effects a transient flow rate rate $Q_t$ as. As it well-known in the present art, the impedance $R_0$ of column 28, in analogy to an electrical system, may be expressed as:

$$R_0 = P_0/Q_0 \qquad (2)$$

where $P_0$ is the system pressure at the constant average flow rate $Q_0$.

Similarly, the time constant T of the system 10 is given by the expression:

$$T = R_0 kV \qquad (3)$$

where $R_0$ is the aforementioned impedance of column 28, $k$ is the compressibility of the liquid 14 in reservoir 12, and V is the volume of reservoir 12.

The "time constant" herein refers to the time for the transient flow rate $Q_t$ to decay to $1/e$ of its maximum value.

In order to appreciate the result achieved by the invention, assume that the velocity v of the piston is altered by $\Delta v$. Then the change in $Q_t$, i.e. $\Delta Q_t$, is $$\Delta Q_t = A \Delta v \qquad (4)$$

where A is the cross-sectional area of piston 20. Since $\Delta v$ is proportional to V and $dP/dt$, $$\Delta v = C_1 V \, dP/dt \qquad (5)$$

and hence $$\Delta Q_t = A C_1 V \, dP/dt. \qquad (6)$$

Hence, the "new" transient flow $Q'_t = Q_t + \Delta Q_t$ is given by:

$$Q'_t = -k V \, dP/dt + C_2 V \, dP/dt \qquad (7)$$

where $C_2 = AC_1$, or $$Q'_t = kV\, dP/dt\, [C_2/k + 1]$$

By comparing equations (1) and (3) with equation (8), it can be seen that the "new" time constant T' for the system with modified piston velocity, becomes $$T' = T(1 - c/k), \tag{9}$$

where c is a proportionality constant which may be set by positioning arm 62 in relation to the compressibility k of liquid 14. Thus, in accordance with the invention, the system time constant may be arbitrarily reduced, subject, limitations in measuring the derivative $dP/dt$ — as will be hereinbelow discussed.

As has previously been indicated, the present invention is particularly applicable to an L.C. system of the type adapted to operate in a gradient elution mode. Thus in FIG. 2, a highly schematic showing is set forth, depicting a system 70 of the type indicated, i.e., one operating in a gradient elution mode. The system 70 differes in its mode of operation from that of FIG. 1, primarily in that instead of a single cylinder and piston pump as in FIG. 1, a pair of such pumps 72 and 74 are utilized. These pumps, in each instance, may be deemed similar to the pump described in connection with FIG. 1, i.e., they are "syringe pumps" comprising cylindrical reservoirs 76 and 78 of volume $V_1$ and $V_2$, in which pistons 80 and 82 unidirectionally advance, to provide their respective solvents through lines 84 and 86 to a mixer 88. Mixer 88 is conventional, and as is known in this art serves to thoroughly blend the two solvents together, with the mixed solvents then being furnished via a line 90 to the chromatographic column 28. In this FIG. 2 elements corresponding to those previously discussed (as, for example, the column 28) are identified by corresponding reference numerals.

Thus again, in FIG. 2, a pressure sensor 36 is provided, which may be of the type discussed in connection with FIG. 1. Sensor 36 in this instance is seen to be placed in the line 90 between mixer 88 and the input to column 28. The output signal from sensor 36 is differentiated at 91 and then furnished by a line 92 to amplifier control logic 94, which is also provided with inputs via lines 96 and 98 from piston position indicator means 100 and 102. The signals thus provided through lines 96 and 98 may be regarded as proportional to the volumes $V_1$ and $V_2$ of reservoirs 76 and 78 at a given time. Thus, these signals may be derived in the manner discussed in connection with FIG. 1.

Amplifier control logic 94 furnishes control signals through lines 108 and 110 to two amplifiers 104 and 106, with the feedback signals from the amplifiers then being furnished to the piston drives 112 and 114 for each syringe pump. Again, this operation is analogous to the mechanism that has been described in connection with FIG. 1. It may be noted further, however, that the precise control scheme for the amplifiers as set forth in FIG. 1 need not be utilized. For example, amplifiers 104 and 106 may be of the variable gain type, with the gain being programmed to follow the volumes $V_1$ and $V_2$ of the reservoirs, as such volumes are indicated by the signals in lines 96 and 98. The volume signal, again, need not be derived precisely as set forth in connection with FIG. 1. For example, the drives 112 and 114 for the pumps may consist of stepping motors, in which event the volumes may be determined by summing the pulses preceding to the stepping motor drive. Such techniques are quite well-known in the art.

Figure 2:
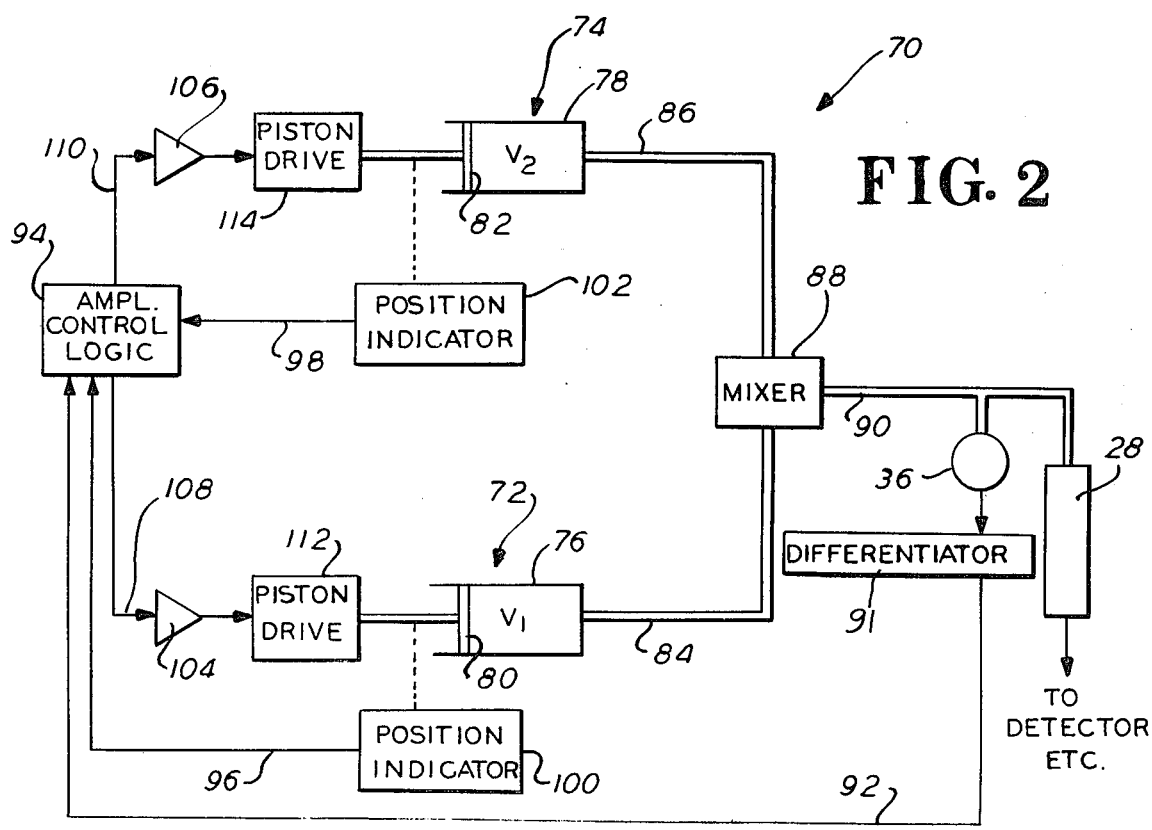
FIG. 2 schematically illustrates a gradient liquid chromatography system, wherein each pump is driven as in the FIG. 1 depiction.

It may also be pointed out that the schematic depiction of FIG. 2 does not explicitly show certain well-known elements normally present in gradient elution systems of the present type. For example, and as is well-known in this art, the piston drives 112 and 114 may also be under the control of a solvent control logic block adjusts the advance rates of the pistons for successive time intervals, as aforementioned to provide desired solvent ratios in accordance with a pre-selected program.

For the single pump sytem of FIG. 1, if the flow rate from the piston is changed from $Q_1$ to $q_2$ in a single step, the flow rate through column becomes $$Q = Q_1 + (Q_2 - Q_1)(1 - e^{-t/T}).$$

If T' is sufficiently short, the flow rate through the column approximates the programmed step, and the compressibility of the fluid is overcome.

For the dual-pump gradient system of FIG. 2, the same consideration holds, where now $$T = T_1 + T_2 \tag{11}$$

such that $T_1 = k_1 V_1 R_0$, and $T_2 = k_2 V_2 R h d\, 0$, where $k_1$ and $k_2$ are the compressibilities of the solvents in reservoirs 76 and 78, respectively. In general, $$T' + T_1[1 - C_3/k_1] + T_2[1 - C_4/k_2],$$

where $C_3$ and $C_4$ are the velocity feedback proportionality constants for the two pistons. If $C_3/k_{1} + C_4/k_2 = c/k$, then $T' = T[1 - c/k]$ as in equation (9). In addition, as explained above, when the fluid visocity varies with concentration of the mixture, unstable oscillations may result. It may then be shown that the system 70 will be stable if $$\tau_m/T' > |1/P\, \delta P/\delta\gamma| - 1$$

Where $\tau_m$ is the volume exchange time of mixer 88, and $\gamma$ and P are the steady state concentration and pressure taken from the curve of pressure vs. Concentration (i.e. viscosity) at the column, at constant flow rate $Q_0$. Equation (12) shows that oscillations can occur if $|1/P\, \delta P/\delta\gamma| > 1$. For example, with a mixture of 99% methanol and 1% water, $|1/P\delta P/\delta\gamma| \approx 4.6$. In this case, the system 70 is stabilized if $\tau_m/\tau' > 3.6$, according to this invention.

The form of equation (12) arises from a perturbation analysis of system 70. In the water-methanol system, the instability is sinusoidal with a period about equal to twice the fluid transit time from the mixer to the column. In the hexane-isopropanol system, the instability has a different form, such that the period is approximately equal to $(T'\tau_m)^{1/2}$. In both cases, equation (12) applies. Since the instability is driven by the compression in the reservoirs, a reduction in T' as indicated in equaton (12) must lead to stability.

Experimentally, it is not possible to measure the instantaneous value of $dP/dt$. Two adjacent points on the $P(t)$ curve are required, and this entails a small time delay $\tau_e$. This delay limits the smallest value of T', such that $T' \sqrt{T\, \tau_e}$. It is easy to make $\tau_e \approx 1$ sec., whereas T is typically several minutes in value. Thus, it is possible to obtain a substantial reduction in the dynamic time constant T'.

While the present invention has been particularly set forth in terms of specific embodiments thereof, it will be understood in view of the present disclosure, that numerous variations upon the invention are now enabled to those skilled in the art, which variations yet reside within the teaching of the invention.

Thus, while the invention has been particularly described in the context of L.C. systems based upon syringe pumps, the invention is applicable to other types of pumps and pumping systems wherein a pump drives fluid through a reservoir. In particular, principles of the invention remain applicable in these further cases, i.e., the derivation $dP/dt$ is determined for the system reservoir and a feedback signal proportional to $dP/dt$ is provided to the pump drive to alter the flow rate from the reservoir, thereby effectively reducing the compressibility of the liquid in the reservoir.

Accordingly the invention is to be broadly construed, and limited only by the scope and spirit of the claims now appended hereto.

I claim:

1. In a liquid chromatography system of the type including a chromatographic column, a reservoir defining a variable volume for containing a slightly compressible mobile liquid phase, piston means cooperating with said reservoir for enabling pumping of said liquid phase through said chromatographic column, and means for normally driving said piston means at a preselected velocity; a method for reducing the effective systemtime constant incident to reattainment of equilibrium pressure and flow, to thereby damp the oscillatory behavior following a change in fluid pressure in said system; said method comprising:

superimposing upon said piston motion an additional velocity component proportional to the time derivative of pressure at said reservoir, and to the volume of said reservoir; to thereby damp the transient oscillations generated by compression of said liquid phase in response to said fluid pressure change.

2. A method in accordance with claim 1, wherein the proportionality constant relating said superimposed velocity component to said pressure derivative and reservoir volume is approximately equal to the compressibility of said liquid phase.

3. A method in accordance with claim 1, including the steps of generating an electrical signal proportional to said system pressure at said reservoir, differentiating said pressure signal, amplifying said differentiated signal in proportion to the volumeof said reservoir, and thereupon utilizing said amplified signal to control the magnitude of the said additional velocity component superimposed upon the motion of said piston means.

4. A method in accordance with claim 1, wherein said system includes a pair of said reservoirs, each reservoir containing a distinct liquid mobile phase, a pair of said piston means, each member of said pair of piston means cooperating respectively with a particular one of said reservoirs, and a pair of said means for driving said piston means; and wherein a distinct additional velocity component is provided to each one of said piston means in proportion to the volume of the particular reservoir interacting with the particular cooperating piston means.

5. A method in accordance with claim 4, wherein each proportionality constant relating a particular one of said superimposed velocity components to said pressure derivative and a particular reservoir volume is approxmately equal to the compressibility of the liquid in said particular reservoir.

6. A method in accordance with claim 4, including the steps of generating an electrical signal proportional to said system pressure acting at said reservoirs, differentiating said pressure signal, providing a pair of amplified signals by amplifying said differentiated signal in proportion to the volume of each of said reservoirs respectively, and thereupon utilizing the pair of amplified signals to control the magnitudes of said additional velocity components superimposed upon each of said piston means.

7. In a liquid chromatography system of the type including a chromatographic column, a reservoir defining a variable volume for containing a slightly compressible mobile liquid phase, piston means cooperating with said reservoir for enabling pumping of said mobile phase through said chromatographic column, and means for normally driving said piston means at a preselected velocity, the improvement enabling reduction of the effective system time constant incident to reattainment of equilibrium pressure and flow, to thereby damp the oscillatory behavior following a change in fluid pressure in said system; said improvement comprising:

means for superimposing upon said piston motion an additional velocity component proportional to the time derivative of pressure at said reservoir and to the volume of said reservoir, whereby to compensate for the transient compressibility of said liquid phase arising from said fluid pressure change.

8. A system in accordance with claim 7, wherein said means for imposing said additional velocity component comprises: a feedback loop including means for generating a signal proportional to said time derivative of the system pressure at said reservoir, means for amplifying said signal in proportion to the volume of said reservoir, and means for coupling the amplified signal in feedback relationship to said piston drive means for driving said piston means at a velocity in proportion to said amplified signal.

9. A system in accordance with claim 8, including means for adjusting the proportionality constant relating said superimposed velocity component to said pressure derivative and reservoir volume, whereby to enable said proportionaltiy constant to be set approximately equal to the compressibility of said liquid phase.

10. A system in accordance with claim 8, wherein said means for generating a signal proportional to said time derivative of system pressure comprises pressure sensing means for detecting said system pressure and converting same into a first electrical signal, and means for differentiating said first electrical signal.

11. A system in accordance with claim 10, wherein said means for amplifying said time derivative signal in proportion to said reservoir volume comprises a slide wire resistance in series with the output from said differentiating means, the position of the slide contact for said resistance being variable in accordance with the position of said piston means.

12. In a liquid chromatography system of the type including a chromatographic column, first and second reservoirs, each reservoir defining a variable volume for containing a distinct slightly compressible liquid solvent, first and second piston means cooperating resepectively with said first and second reservoirs for enabling pumping of said solvents through said chromatographic column, and first and second means for normally driving said first and second piston means respectively at pre-selected velocities; the improvement enabling reduction of the effective system time constant incident to reattainment of equilibrium pressure and flow, to thereby damp the oscillatory behavior following a change in fluid pressure in said system; said improvement comprising:

means for superimposing upon the motion of each of said first and second piston means respectively an additional velocity component proportional to the time derivative of the system pressure acting upon said reservoirs and to the volume of said first and second reservoirs respectively, to thereby damp transient oscillations generated by compression of said solvents in response to said fluid pressure change.

13. A system in accordance with claim 12, including means for generating an electrical signal proportional to said system pressure acting at said reservoirs, means for differentiating said pressure signal, means for providing a pair of amplified signals by amplifying said differentiated signal in proportion to the volume of each of said reservoirs respectively, and means for utilizing the resulting pair of amplified signals to control the magnitudes of said additional velocity components superimposed upon each of said piston means.

14. In a liquid chromatography system of the type including a chromatographic column, a reservoir defining a variable volume for containing a mobile liquid phase, pumping means cooperating with said reservoir for enabling pumping of said liquid phase through said chromatographic column, and means for normally driving said pumping means at a pre-selected pumping rate; the method for reducing the effective time constant incident to reattainment of equilibrium pressure and flow, to therby damp the oscillatory behavior following a change in fluid pressure in said system; said method comprising superimposing upon said pre-selected pumping rate an additional pumping rate component proportional to the time derivative of pressure at said reservoir and to the volume of said reservoir, to thereby damp the transient oscillations generated by compression of said liquid phase in response to said fluid pressure change.

15. A method in accordance with claim 14, wherein the proportionality constant relating said superimposed additional pumping rate component to said pressure derivative and reservoir volume is approximately equal to the compressibility of said liquid phase.

16. In a system for providing precise liquid flow rate control, an apparatus for pumping a liquid through a conduit at a substantially constant flow rate, where the flow rate is changeable in response to a factor other than a variation in an operating parameter of said apparatus, said appparartus comprising an enclosed reservoir defining a variable volume for said liquid, pumping means for drawing said liquid into said reservoir, said reservoir havng an exit port for the passage of said liquid therefrom into said conduit, means for generating a $dP/dt$ signal indicative of the first derivative with respect to time of the pressure of said liquid in said reservoir, means for scaling said $dP/dt$ signal so as to provide a V $dP/dt$ correction signal proportional to the product of said $dP/dt$ signal and the volume of said reservoir, and means for causing the pumping speed of said pumping means to vary in response to variations in said correction signal.

17. The apparatus of claim 16 wherein the volume of said reservoir comprises the fluid-containing volume connecting said pumping means to said conduit.

18. The apparatus of claim 16 wherein said conduit comprises a chromatographic column.

19. The apparatus of claim 16 wherein said factor in response to which the flow rate is changeable is the compressibility of said fluid.

20. The apparatus of claim 16 wherein said reservoir and pumping means are provided by a syringe pump.

21. The apparatus of claim 16 wherein said means for generating said $dP/dt$ signal comprises means for sensing the pressure of said fluid in said reservoir and for generating a first electrical signal indicative of said pressure, and means for differentiating said first electrical signal.

22. The apparatus of claim 21 wherein said pressure sensing means comprises a strain gauge.

23. The apparatus of claim 20 wherein said means for scaling said $dP/dt$ signal so as to provide said correction signal comprises a slide wire resistance in series with the output of said means for generating said $dP/dt$ signal, the position of the slide contact of said slide wire resistance being variable in accordance with the stroke of said pump.

24. In a liquid chromatography system comprising a chromatographic column, first and second reservoirs, first and second piston means, said first piston means being able to cooperate with said first reservoir to enable pumping action to cause pumping of a first liquid phase from said first reservoir into a mixing region, and said second piston means being able to cooperate with said second reservoir to enable pumping action to cause pumping of a second liquid phase from said second reservoir into said mixing region wherein said second liquid phase can mix with said first liquid phase, the pumping actions enabled by the cooperation of said first and second piston means with said first and second reservoirs, respectively, enabling the mixture of said first and second liquid phases to enter said chromatographic column, first and second driving means, said first driving means being able to drive said first piston means at a preselected first velocity, and said second driving means being able to drive said second piston means at a preselected second velocity, a method for reducing the effective system time constant incident to reattainment of equilibrium pressure and flow, thereby to damp oscillatory behavior following a change in fluid pressure in said system, said method comprising:

superimposing upon the motion of each one of said piston means a distinct additional velocity component, said additional velocity component being proportional to the product of the volume of the particular reservoir that cooperates with the particular piston means, and the time derivative of the pressure at a location between said mixing region and said chromatographic column, the magnitudes of the additional velocity components being controlled by the steps of:

generating an electrical signal proportional to the pressure at said location between said mixing region and said chromatographic column, differentiating said pressure signal, providing a pair of amplified signals, one of said amplified signals being obtained by amplifying said differentiated signal in proportion to the volume of said first reservoir, and the other of said amplified signals being obtained by amplifying said differentiated signal in proportion to the volume of said second reservoir, and utilizing said pair of amplified signals to control the magnitudes of said additional velocity components.

* * * * *